United States Patent [19]

Berg et al.

[11] 4,410,544

[45] Oct. 18, 1983

[54] PLATINUM-DIAMINE COMPLEXES, A METHOD FOR THE PREPARATION OF A MEDICINE USING SUCH A PLATINUM-DIAMINE COMPLEX FOR THE TREATMENT OF MALIGNANT TUMOR IN MICE

[75] Inventors: Jan Berg, Nieuwegein; Francois Verbeek, Harmelen; Eric J. Bluten, Blaricum, all of Netherlands

[73] Assignee: Nederlandse Centrale Organisatie voor Toegespastnatuurwetenschappeli-ukonderzoek, Juliana van Stolberglaan, Netherlands

[21] Appl. No.: 287,531

[22] Filed: Jul. 27, 1981

Related U.S. Application Data

[63] Continuation-in-part of Ser. No. 54,891, Jul. 5, 1979, abandoned.

[30] Foreign Application Priority Data

Jul. 6, 1978 [NL] Netherlands ..................... 7807334

[51] Int. Cl.³ ...................... C07F 15/00; A61K 31/28
[52] U.S. Cl. .................................. 424/287; 260/429 R
[58] Field of Search ..................... 260/429 R; 424/287

[56] References Cited

U.S. PATENT DOCUMENTS 3,892,790  7/1975  Tobe et al. ..................... 260/429 R
3,904,663  9/1975  Tobe et al. ..................... 260/429 R
4,140,707  2/1979  Cleare et al. .................. 260/429 R

OTHER PUBLICATIONS

Appleton, T. G.; Hall, J. R., *Inorganic Chemistry*, vol. 11, No. 1, p. 112, 1972.
Appleton, T. G., Hall, J. R., *Inorganic Chemistry*, vol. 9, No. 8, p. 1800, 1970.
*Chemical Abstracts*, vol. 80, p. 4, ref. 66593d.
*Chemical Abstracts*, vol. 87, 1977, p. 11, ref. 15694z.
*Chemical Abstracts*, vol. 87, ref. 145547q, p. 14.
*Chemical Abstracts*, vol. 78, 1973, p. 10, ref. 105899p.
Bioinorg. Chem. 2, 187–210, (1973).
Platinum Metal Reviews 17, 2–13, (1973).
Cleare, M. J. and Hoeschele, J. D., *Platinum Metals Rev.* 17, (1), 1973.

*Primary Examiner*—Helen M. S. Sneed

*Attorney, Agent, or Firm*—Brumbaugh, Graves, Donohue & Raymond

[57] ABSTRACT

This invention relates to novel platinum-diamine complexes having the formula:

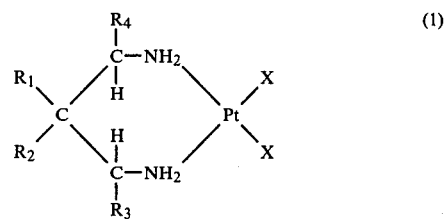

(1)

wherein $R_1$ and $R_2$ independently of each other may be selected from the group consisting of hydrogen, an alkyl group having 1–20 carbon atoms, a cycloalkyl group having from 3–7 carbon atoms in the ring, an aralkyl group, and an aryl group having 1–20 carbon atoms, whereas $R_1$ and $R_2$ together may form a cycloalkyl group having 3–7 carbon atoms in the ring and having the formula:

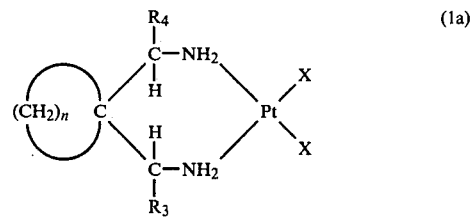

(1a)

wherein N is 2 to 7 and wherein $R_3$ and $R_4$ independently of each other are selected from the group consisting of hydrogen, an alkyl group having 1–20 carbon atoms, an aryl group or an aralkyl group having 1–20 carbon atoms in the alkyl group and X is an anionic group, providing that when X is either chlorine or malonate, $R_1$, $R_2$, $R_3$ and $R_4$ are not each H; when X is chlorine and $R_1$ and $R_2$ are each H, $R_3$ and $R_4$ are not each methyl; when X is chlorine and $R_1$ and $R_2$ are each methyl, $R_3$ and $R_4$ are not each H, and when X is chlorine $R_1$ is hydrogen and $R_2$ is methyl and $R_3$ and $R_4$ are not each hydrogen.

29 Claims, No Drawings

PLATINUM-DIAMINE COMPLEXES, A METHOD FOR THE PREPARATION OF A MEDICINE USING SUCH A PLATINUM-DIAMINE COMPLEX FOR THE TREATMENT OF MALIGNANT TUMOR IN MICE

This application is a continuation-in-part of application Ser. No. 054,891 filed July 5, 1979 now abandoned.

The invention relates to novel platinum-diamine complexes, and to a pharmaceutical composition using such a platinum-diamine complex for the treatment of mice, for example, malignant swellings and malignant tumors in mammals.

Platinum-diamine complexes are known from the article by A. P. Zipp and S. G. Zipp, J. Chem. Ed., 54 (12) (1977), page 739, which describes the application of cis-platinum diamine dichloride (PDD) for the treatment of cancer. It is known that platinum compounds have a broad spectrum of activity as antitumor agents, but also that they have serious drawbacks, in particular that they are toxic to the kidneys. Cis-platinum diamine dichloride is often used in combination with another substance or administered with large quantities of liquid or other techniques are used to bring about an adequate flow-through of the kidneys, as a method for counteracting kidney toxicity. A number of other platinum amine complexes are known including compounds having the formula:

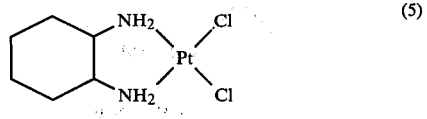

(5)

Wadley Medical Bulletin, Vol. 7, No. 1, pp. 114-134, discloses a large number of platinum diamine complexes, including cis platinum diamine dichloride, for the treatment of cancer. Here, too, the kidney toxicity is stated as the most important drawback of these compounds.

Chem. and Eng. News, 6th June 1977, pp. 29-30, also describes cis-platinum diamine dichloride and its application for the treatment of cancer. Kidney toxicity is also mentioned as the most important drawback of these compounds.

In an article in Cancer Chemotherapy Reports Part 1, Vol. 59, No. 3, May/June 1975, pp. 629-641. The kidney toxicity of cis-platinum diamine dichloride is also reported. Because of the toxicity of PDD to the kidney and its low therapeutic index, other platinum complexes for the treatment of cancer have been sought. For this purpose combinations of cis-platinum diamine dichloride with other chemotherapeutic agents were tested. Novel platinum complexes were also tried, but they were also found to be too toxic. It was found, for instance, that although cis-dichlorobiscyclopentyl amine platinum(II) is only slightly toxic to the kidneys, it is toxic to the spleen. So-called "platinum blues", a mixture of different amounts of five or more inseparable components have also been disclosed for the treatment of cancer.

Dutch Patent Applications Nos. 73,04880; 73,04881; 73,04882 and 77,03752 disclose a large number of platinum diamine complexes, including the compound having formula (5) above. In all of these compounds with a nucleus, nitrogen atoms are linked directly to the nucleus. The compounds of the first three Dutch applications were compared with cis-platinum diamine dichloride and were found to have better effects. None of the patent applications states anything about toxicity.

Toxicity is a very serious drawback of PDD, as well as all other anti-cancerous platinum complexes that have been used so far. The high toxicity of these compounds, especially the kidney toxicity which is the most dangerous one, actually limits the dose of the drug that can be given to a subject.

In spite of the considerable research in this field prior to this invention, no one has succeeded in developing compounds with anti-cancerous activity comparable to that of PDD, but with significantly lower toxicity, especially kidney toxicity.

Novel platinum diamine complexes have now been found that are suitable for the treatment of mice in mammals and that display little or no kidney toxicity.

The platinum diamine complexes according to the invention are characterized by the formula:

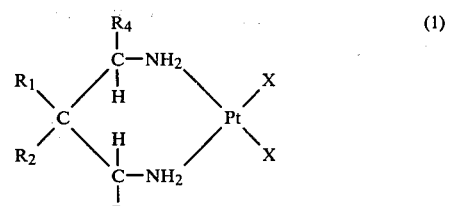

(1)

wherein $R_1$ and $R_2$ independently of each other may be selected from the group consisting of hydrogen, an alkyl group having 1-20 carbon atoms, a cycloalkyl group having from 3-7 carbon atoms in the ring, an aralkyl group, and an aryl group, whereas $R_1$ and $R_2$ together may form a cycloalkyl group having 3-7 carbon atoms in the ring and having the formula:

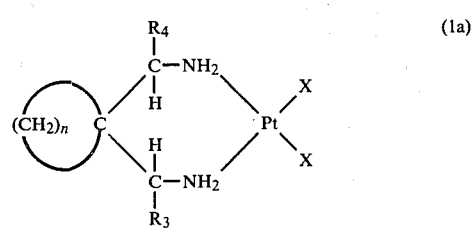

(1a)

wherein n is 2 to 7 and wherein $R_3$ and $R_4$ independently of each other are selected from the group consisting of hydrogen, an alkyl group having 1-20 carbon atoms, an aryl group or an aralkyl group having 1-20 carbon atoms in the alkyl group and X is an anionic group, providing that when X is either chlorine or malonato, $R_1$, $R_2$, $R_3$ and $R_4$ are not each H; when X is chlorine and $R_1$ and $R_2$ are each H, $R_3$ and $R_4$ are not each methyl; when X is chlorine and $R_1$ and $R_2$ are each methyl, $R_3$ and $R_4$ are not each H, and when X is chlorine $R_1$ is hydrogen and $R_2$ is methyl and $R_3$ and $R_4$ are not each hydrogen.

Compounds having the following formula:

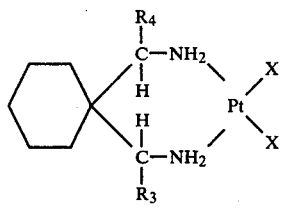
(2)

in which R₃, R₄ and X has the same meaning as in formula 1 are preferred, for example, cis-dichloro-1,1-di(aminomethyl)cycloalkyl platinum(II), having the formula:

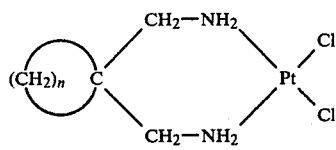
(3)

wherein n is 2–7, preferably 3–5 and cis-dichloro-1,1-di(aminomethyl)cyclohexyl platinum(II) having the following formula:

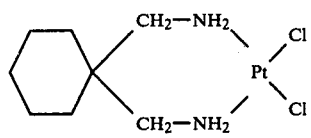
(4)

In formulas 1–2 the anionic group X preferably is a chlorine, bromine or iodine, sulphate, phthalate, acetate, carboxylate, an oxalate, malonate or substituted malonate group and isocitrate. The acetate can be, for example, chloroacetate. The substituents on a malonate group could be, for example, hydroxy or ethyl.

The invention further relates to a pharmaceutical composition in which these novel compounds are used as the active ingredient. In preparing the pharmaceutical compositions, the novel compounds are mixed with known liquid or solid carriers to form injectable liquids or oral preparations.

An extensive research program carried out by the National Cancer Institute, Bethesda, Md., and the European Organization for Research on the Treatment of Cancer, Brussels, Belgium, has shown that when compared to PDD, compounds according to this invention, particularly compounds having the following formulas display a high therapeutic activity against a great number of different mammalian types of tumor, such as P 388 lymphocytic leukemia (PS), L-1210 lymphoid leukemia (LE), ependymoblastoma (EM), B 16 melanocarcinoma (B₁) and a line of L-1210 leukemia resistant to cis-PDD (LE/cis-PDD):

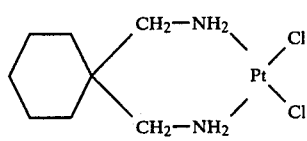
(4)

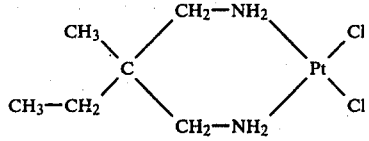
(8)

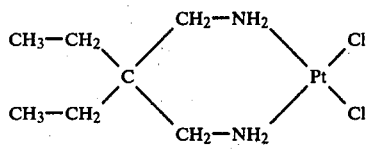
(9)

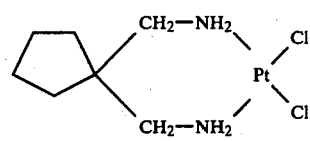
(10)

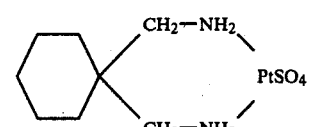
(11)

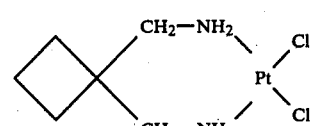
(12)

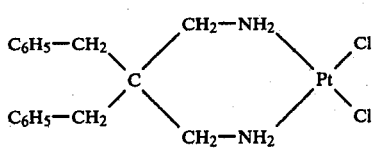
(13)

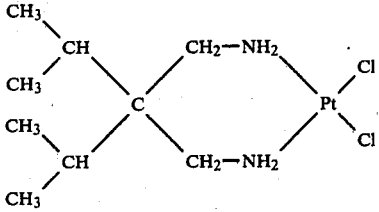
(14)

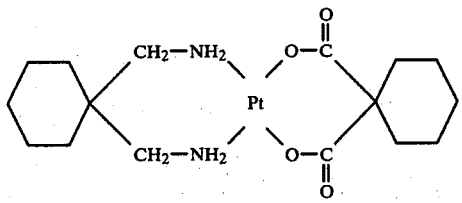
(7)

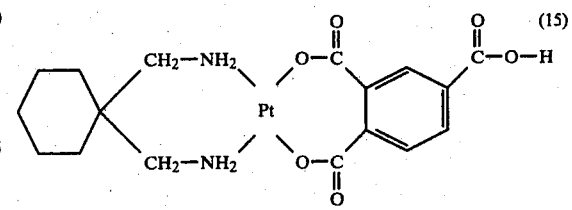
(15)

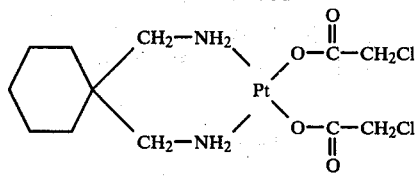
(16)

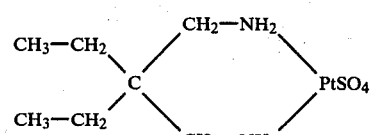
(17)

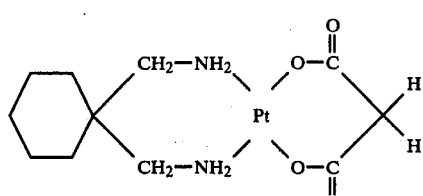
(18)

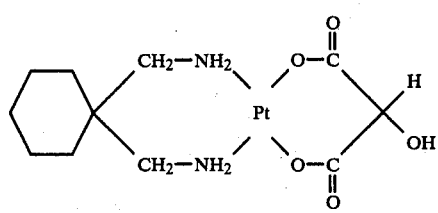
(19)

The results of these experiments are set forth in Table A. It is important to note that compounds, such as those having formulas 17, 18 or 19 appeared to be even more effective against the cis-PDD resistant line of L-1210 than they are against the parent line of L-1210. In several cases complete cures were observed with the novel compounds, an effect which was not observed with cis-PDD.

More detailed information concerning the testing procedure and their interpretation are contained in Instruction 14, Screening Data Summary, Interpretation and Outline of Current Screen, Drug Evaluation Branch, National Cancer Institute, Bethesda, Md., 20014 (1977) which is incorporated herein by reference.

TABLE A.

Anti-cancerous activity in mice

| Compound | Mouse Code | Tumor | Dose/injection (mg/kg) | T/C* (%) |
|---|---|---|---|---|
| Formula 4 | $CD_2F_1$ | PS | 6.25 | 201 |
|  |  |  | 3.12 | 181 |
|  |  |  | 1.56 | 153 |
| Formula 4 | $CD_2F_1$ | LE | 12.50 | 234 |
|  |  |  | 6.25 | 180 |
|  |  |  | 3.12 | 145 |
| Formula 4 | C57BL/6 | EM | 6.00 | 126 |
| Formula 4 | $B_6D_2$ (BDF) | BI | 6.00 | 208 |
|  |  |  | 3.00 | 208 |
|  |  |  | 1.50 | 190 |
| PDD | $B_6D_2$ (BDF) | BI | 2.00 | 197 |
| Formula 7 | $CD_2F_1$ | PS | 25.00 | 226 |
|  |  |  | 12.50 | 177 |
|  |  |  | 6.25 | 162 |
| Formula 7 | $CD_2F_1$ | LE | 80.00 | 138 |
| Formula 7 | 57BL/6 | EM | 12.50 | 163 |
|  |  |  | 6.25 | 130 |
| Formula 8 | $CD_2F_1$ | LE | 12.50 | 289 |

TABLE A.-continued

Anti-cancerous activity in mice

| Compound | Mouse Code | Tumor | Dose/injection (mg/kg) | T/C* (%) |
|---|---|---|---|---|
| Formula 9 | $CD_2F_1$ | LE | 12.50 | 323 |
| Formula 11 | $CD_2F_1$ | LE | 12.50 | 274 |
| Formula 10 | $CD_2F_1$ | LE | 12.50 | 148 |
| Formula 12** | $BDF_1$ | LE | 15.00 | 208 |
| Formula 13 | $BDF_1$ | LE | 50.00 | 135 |
| Formula 14 | $BDF_1$ | LE | 50.00 | 178 |
| Formula 15 | $BDF_1$ | LE | 40.00 | 200 |
| Formula 16 | $BDF_1$ | LE | 6.00 | 207 |
| Formula 17 | $BDF_1$ | LE | 12.00 | 200 |
| Formula 17 | $BDF_1$ | LE/cis PDD | 6.00 | >500 (3/6) |
| Formula 18 | $BDF_1$ | LE | 64.00 | 200 (1/6) |
| Formula 18 | $BDF_1$ | LE/cis PDD | 16.00 | 230 |
| Formula 19 | $BDF_1$ | LE | 36.00 | 246 |
| Formula 19 | $BDF_1$ | LE/cis PDD | 24.00 | >500 (3/6) |
| Cis PDD | $BDF_1$ | LE | 8.00 | 183 |
| Cis PDD | $BDF_1$ | LE/cis PDD | 4–8 | 106–121 |

*Period of survival is the ratio of survival times of the treated mice (T) to untreated mice (C); the therapeutic activity is significant at T/C ≧ 125. The figures include dying mice only. A cure is defined as a mouse free of tumors 45 days after injection, as determined by visual inspection at autopsy.
**For Formula 12--cis PDD the mice were injected with $10^6$ L-1210 ascites cells. One I.P. injection of the test compound was given to each of six mice.

TABLE B.

Percentage of urea-nitrogen in the blood after administering platinum complexes (in the rat).

| Compound | Dose (mg/kg) | Number of days after injection | Percentage of urea-nitrogen in blood |
|---|---|---|---|
| Formula 4 | 8($LD_{10}$) | 0 | 10 |
|  |  | 2 | 10 |
|  |  | 4 | 15 |
| Formula 4 | 15($LD_{50}$) | 0 | 10 |
|  |  | 2 | 15 |
|  |  | 4 | 17 |
| Controls | — | 0 | 10 |
|  |  | 2 | 9 |
|  |  | 4 | 11 |
| √PDD | 3($LD_{10}$) | 0 | 10 |
|  |  | 2 | 13 |
|  |  | 4 | 52 |
|  | 7.6($LD_{50}$) | 0 | 10 |
|  |  | 2 | 78 |
|  |  | 4 | 148 |

Blood urea nitrogen (BUN) levels were also evaluated for the mice treated with compounds having formulas 12–19 on 4, 7 and 11 days after drug administration. In comparison with rats treated with cis-PDD, none of the compounds having formulas 12–19 caused a significant elevation of the BUN values.

The data in Table B demonstrate that compounds according to this invention do not have any effect on the urea-nitrogen content in the blood (BUN). Both at doses corresponding with the $LD_{10}$-amount and at those corresponding with the $LD_{50}$-amount the urea-nitrogen contents in the blood are identical to the control values. BUN values ≧ 30 mg% are generally considered indicative of drug-induced nephrotoxicity. In contrast, PDD at a $LD_{10}$-dose, 4 days after injection, caused about a quadruple increase in the urea nitrogen content. In was found by means of a histological examination of rats after treatment with toxic doses of compounds of this invention, that these compounds display little or no kidney toxicity.

The preparation of the compounds listed in Tables A and B are shown in the following examples.

The compounds were prepared according to the method by S. C. Dhara; Indian J. Chem. 8, 193 (1970).

EXAMPLE 1

Cis-diiodo-1,1-di(aminomethyl)cyclohexane platinum(II) (6) having the formula:

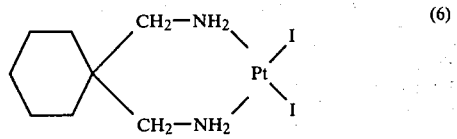

To a solution of 16 g K₂PtCl₄ in 160 ml of water a solution of 26.4 g KI in 20 ml of water were added and the mixture was heated for 5 min. in a water bath.

Hereupon 6.4 g 1,1-di(aminomethyl)cyclohexane were added and after the mixture had been stirred for 5 minutes, the precipitate was sucked and washed three times with hot water, twice with cold ethyl alcohol and twice with ether.

Yield 22.1 g.

EXAMPLE 2

Cis-dichloro-1,1-di(aminomethyl)cyclohexane platinum(II) (4)

11.8 g of the diiodo derivative, prepared according to Example 1, were added to a solution of 6.6 g AgNO₃ in 48 ml water.

After the mixture had been stirred for 10 minutes at 95°–100° C., the AgI was filtered off and washed with water. To the clear filtrate 3.28 g KCl were added and the mixture was stirred for 12 min. at 95°–100° C. After the mixture had been cooled, the precipitate was sucked and washed with water.

Yield: 6.0 g.

Analysis (percentage by weight): Calcul.: C: 23.53; H: 4.45; N: 6.87; Pt: 47.80; Found: C: 23.32; H: 4.46; N: 6.86; Pt: 47.63.

EXAMPLE 3

Cis-cyclopentamethylene malonato-1,1-di(aminomethyl)cyclohexane platinum(II) (7)

20.65 g the diiode derivative, prepared according to Example 1, were added to a solution of 11.55 g AgNO₃ in 85 ml of water.

After the solution had been stirred for 10 minutes at 95°–100° C., the AgI was filtered off and washed with water. When the filtrate was still hot, a solution of 5.0323 g cyclopentamethylene malonic acid in 114.34 ml 0.51125 N NaOH were added and the mixture was heated for 12 min. at 95°–100° C. After the mixture had been cooled, the precipitate was sucked and washed with water. After drying under reduced pressure the product obtained was extracted with 4 l methanol, the methanol solution was treated with activated carbon, filtered until it was clear and the filtrate evaporated to dryness under reduced pressure. The residue was suspended in 500 ml alcohol, sucked off and washed with methanol.

Yield 4.75 g.

Analysis (percentage by weight): Calcul.: C: 37.86; H: 5.56; N: 5.52; Pt: 38.46. Found: C: 37.50; H: 5.50; N: 5.60; Pt: 38.19.

Analogous to Examples 1 and 2, the following compounds were prepared, which are very pale yellow crystalline substances.

EXAMPLE 4

Cis-dichloro-(2-methyl-2-ethyl)-1,3-propane diamine platinum (II) (8) having the formula

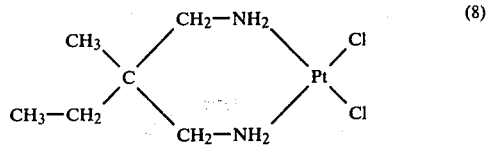

Yield: 55% by weight.
Analysis (% by weight): Calcul.: C: 18.86; H: 4.22; N: 7.33; Pt: 51.04; Cl: 18.55. C: 18.73; H: 4.14; N: 7.26; Pt: 51.33; Cl: 18.69.

EXAMPLE 5

Cis-dichloro-2,2-diethyl-1,3-propane diamine platinum(II) (9) having the formula:

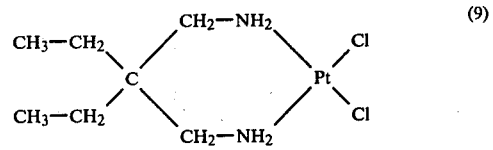

Yield: 70% by weight.
Analysis (% by weight): Calcul.: C: 21.22; H: 4.58; N: 7.07; Pt: 49.24; Cl: 17.89. C: 21.04; H: 4.50; N: 7.02; Pt: 49.43; Cl: 17.83.

EXAMPLE 6

Cis-dichloro-1,1-di(aminomethyl)cyclopentane platinum(II) (10) having the formula:

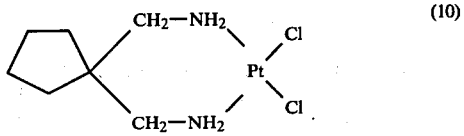

Yield: 70% by weight.
Analysis (% by weight): Calcul.: C: 21.33; H: 4.09; N: 7.11; Pt: 49.49; Cl: 17.98; Found: C: 21.36; H: 4.10; N: 7.14; Pt: 49.27; Cl: 17.91.

EXAMPLE 7

Cis-1,1-di(aminomethyl)cyclohexane platinum(II) sulphate (11) having the formula:

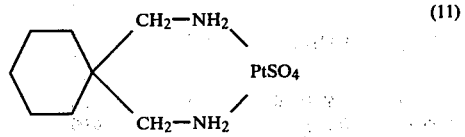

2 g diiodo derivative, prepared as in Example 1, were suspended in 150 ml water. After stirring during 20 hours with 1.0 g Ag₂SO₄ the AgI was filtered off and washed with H₂O. The clear filtrate was evaporated.

Yield: 1.1 g ~80% by weight.
Analysis (% by weight): Calcul.: C: 22.17; H: 4.19; N: 6.46; Found: C: 22.02; H: 4.62; N: 6.31.

The following compounds in Examples 8 to 10 were prepared according to the Method of G. L. Johnson: Inorg. Synth. VIII, pp. 242–244.

EXAMPLE 8

Cis-dichloro-1,1-di(aminomethyl)cyclobutane platinum(II) (12) having the formula:

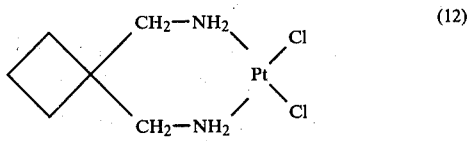
(12)

2.8 g 1,1-di(aminomethyl)-cyclobutane, 2 g HCl and 6.2 g K$_2$PtCl$_4$ were dissolved in 50 ml water, heated to 95°–100° C. and to this 1.2 g NaOH in 25 ml water were dropwise added so quickly that the pH was maintained at ±6.

The precipitate formed was sucked, washed with water and dried. The product was taken up in 250–300 ml aqueous NH$_3$ and filtered. After evaporating NH$_3$ the product was washed with 2 N HCl, water and dried.

Yield: 3.7 g ~65% by weight.

Analysis (% by weight): Calcul.: C: 18.96; H: 3.71; N: 7.37; Pt:51.31; Cl: 18.65; Found: C: 18.95; H: 3.67; N: 7.37; Pt: 51.02; Cl: 18.47.

EXAMPLE 9

Cis-dichloro-2,2-dibenzyl-1,3-propane diamine platinum(II) (13)

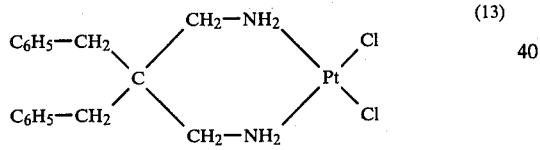
(13)

Yield: 45% by weight.

Analysis: (% by weight): Calcul.: C: 39.24; H: 4.26; N: 5.38; Found: C: 39.81; H: 4.38; N: 5.73.

EXAMPLE 10

Cis-dichloro-2,2-diisopropyl-1,3-propane diamine platinum(II) (14)

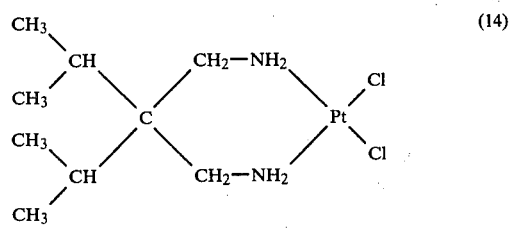
(14)

Prepared as in Example 9.
Analysis (% by weight):
Calcul.: C: 25.48; H: 5.23, N: 6.60. Found: C: 26.31; H: 5.39; N: 6.90.

EXAMPLE 11

Cis-4-carboxyphthalato-1,1-di(aminomethyl)-cyclohexane platinum (II) having formula 15

1.2 g of the dichloro derivative prepared according to Example 2 (formula 4), were added to a solution of 1 g AgNO$_3$ in 25 ml of water.

After the mixture has been stirred for 1 h. at 40° C. the AgCl was filtered off and washed with water.

To the clear filtrate 0.63 g of 1,2,4-tricarboxybenzene were added and the mixture was stirred for 2 h. at room temperature. The precipitate was sucked and washed with water.

Yield 0.8 g (45% by weight)

Analysis (% by weight): Calcul.: C: 36.24; H: 4.29; N: 4.97; Found: C: 36.42; H: 4.13; N: 4.77.

EXAMPLE 12

Cis-1,1-di(aminomethyl)-cyclohexane-bis(-chloroacetato)platinum(II) having formula 16

1.6 g of the dichloro derivative prepared according to Example 2 (formula 4), were added to a solution of 1.28 g AgNO$_3$ in 25 ml of water.

After stirring the mixture for 1 h. at 40° C. the AgCl was filtered off and washed with water.

To the clear filtrate a solution of 0.73 g of monochloroacetic acid and 0.45 g KOH in 25 ml of water were added and the mixture was stirred for 2 h. at room temperature. The precipitate was sucked and washed with water.

Yield: 1.3 g (65% by weight).

Analysis (% by weight):

Calcul.: C: 27.49; H: 4.23; H: 5.34; Found: C: 27.43; H: 4.21; H: 5.55.

The following compounds were prepared as in Example 7.

EXAMPLE 13

Cis-2,2-diethyl-1,3-propanediamine platinum(II) sulphate having formula 17

Yield: 90% by weight.

Analysis (% by weight): Calcul.: C: 19.95; H: 4.27; N: 6.65; Found: C: 20.06; H: 4.46; H: 6.68.

EXAMPLE 14

Cis-1,1-di(aminomethyl)-cyclohexanemalonato platinum(II) having formula 18

1.6 g of the dichloro derivative prepared according to Example 2 (formula 4), were added to a solution of 1.28 g AgNO$_3$ in 25 ml of water.

After stirring the mixture for 1 h. at 40° C. the AgCl was filtered off and washed with water.

To the clear filtrate a solution of 0.4 g of malonic acid and 0.455 g KOH in 10 ml of water was added.

After stirring for 2 h. at room temperature the precipitate was filtered off and dried.

Yield: 1.0 g (59% by weight).

Analysis (% by weight): Calcul.: C: 30.07; H: 4.59; H: 6.38; Pt: 44.40; O: 14.57; Found: C: 29.98; H: 4.54; H: 6.32; Pt: 44.32; O: 14.57.

EXAMPLE 15

Cis-1,1-di(aminomethyl)cyclohexanehydroxymalonato platinum(II) having formula 19 was prepared according to Example 14

Yield: 77% by weight.

Analysis (% by weight): Calcul.: C: 29.01; H: 4.43; N: 6.15; Pt: 42.84; O: 17.58; Found: C: 28.77; H: 4.38; N: 6.18; Pt: 42.96; O: 17.54.

Compounds having the following formulas not listed in Table A were prepared according to Example 14:

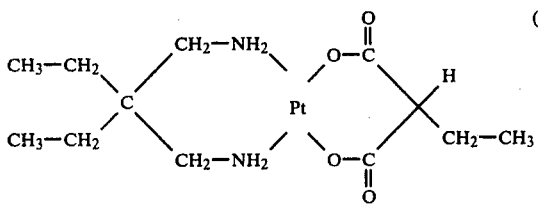
(20)

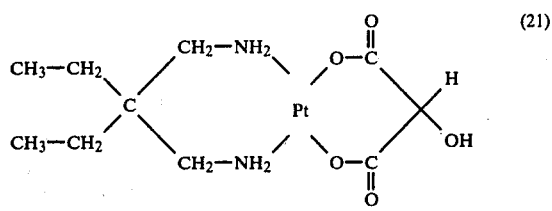
(21)

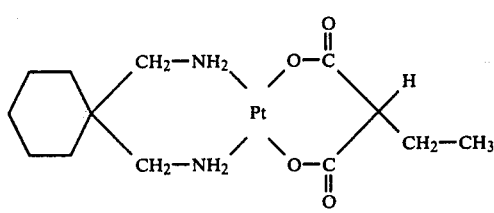
(22)

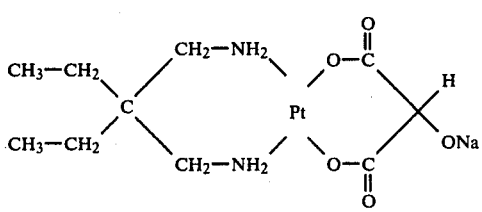
(23)

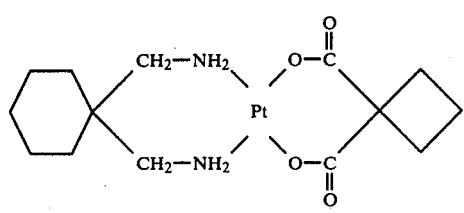
(24)

EXAMPLE 16

Cis-2,2-diethyl-1,3-diaminopropane 2-ethylmalonato platinum(II) having formula 20.

Yield: 65% by weight.
Analysis (% by weight): Calcul. +2H$_2$O: C: 29.33; H: 5.74; N: 5.70; Found: C: 29.23; H: 5.64; N: 5.71.

EXAMPLE 17

Cis-2,2-diethyl-1,3-diaminopropane 2-hydroxymalonato platinum(II) having formula 21

Yield: 87% by weight.
Analysis (% by weight): Calcul. +1/2H$_2$O: C: 26.55; H: 4.68; N: 6.19; Found: C: 26.67; H: 4.56; N: 6.23.

EXAMPLE 18

Cis-1,1-di(aminomethyl)cyclohexane 2-ethyl-malonato platinum(II) having formula 22

Yield: 64% by weight.
Analysis (% by weight): Calcul. +1,5H$_2$O: C: 31.57; H: 5.50; N: 5.67; O:17.79; Pt: 39.43; Found: C: 31.36; H: 5.47; N: 5.69; O: 18.02; Pt: 39.58.

EXAMPLE 19

Cis-2,2-diethyl-1,3-diaminopropane 2-hydroxymalonato platinum(II) sodium salt having formula 23

0.5 g of the hydroxymalonato derivative prepared according to Example 17 (formula 21) were suspended in 25 ml of water.

1.105 ml of 0.1 N NaOH were added and the mixture was stirred for 30 min. at room temperature.

The clear solution was evaporated and the remaining solid dried.

Yield: 0.4 g (72% by weight).
Analysis (% by weight): Calcul. +2H$_2$O: C: 23.91; H: 4.61; N: 5.58; Found: C: 23.75; H: 4.44; N: 5.52.

EXAMPLE 20

Cis-1,1-di(aminomethyl)cyclohexane 1,1-cyclobutanedicarboxylato platinum(II) having formula 24.

2 g of the dichloro compound, prepared according to Example 2 (formula 4) were added to a solution of 1.6 g AgNO$_3$ in 25 ml of water.

After stirring the mixture for 1 h. at 40° C. the AgCl was filtered off and washed with water.

To the clear filtrate a solution of 0.677 g of 1,1-cyclobutanedicarboxylicacid and 0.547 g of KOH in 10 ml of water.

After 2 h. at room temperature and 1 h. at 0° C. the white precipitate was filtered off and dried.

Yield: 1.4 g (62% by weight).
Analysis (% by weight): Calcul. +H$_2$O: C: 33.80; H: 5.27; N: 5.63; Found: C: 33.98; H: 5.02; N: 5.77.

Compounds having the following formulas were prepared as in Example 20:

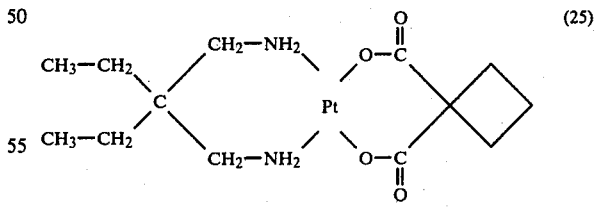
(25)

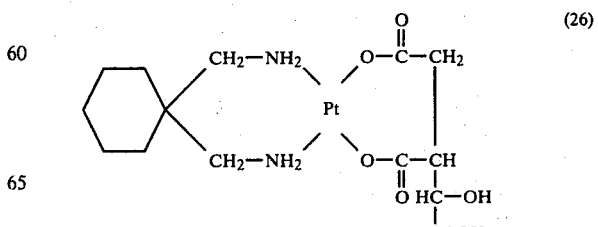
(26)

EXAMPLE 21

Cis-2,2-diethyl-1,3-diaminopropane 1,1-cyclobutanedicarboxylato platinum(II) having formula 25

Yield: 64% by weight.
Analysis (% by weight): Calcul. +2.5H$_2$O: C: 30.46; H: 5.70; N: 5.47; Pt: 38.07; Found: C: 30.40; H: 5.44; N: 5.37; Pt: 38.16.

EXAMPLE 22

Cis-1,1-di(aminomethyl)cyclohexane platinum(II) isocitrate having formula 26

4 g of the dichloro compound, prepared according to Example 2 (formula 4) were added to a solution of 3.2 g AgNO$_3$ in 30 ml of water.

After stirring the mixture for 1 h. at 40° C. the AgCl was filtered off and washed with water.

To the clear filtrate a solution of 2.85 g of DL-isocitric acid di-sodium salt in 15 ml of water were added and the mixture was stirred for 2 h. at room temperature. The precipitate was sucked off and washed with water.

Yield: 3.5 g (68% by weight).
Analysis (% by weight): Calcul: C: 31.88; H: 4.59; H: 5.31; Found: C: 30.8; H: 4.9; H: 5.0.

We claim:

1. Platinum-diamine complexes having the formula:

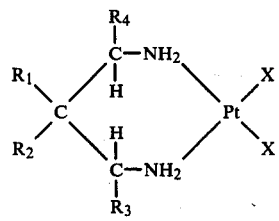

wherein R$_1$ and R$_2$ independently of each other may be selected from the group consisting of hydrogen, an alkyl group having 1-20 carbon atoms, a cycloalkyl group having from 3-7 carbon atoms in the ring, an aralkyl group, and an aryl group having 1-20 carbon atoms, whereas R$_1$ and R$_2$ together may form a cycloalkyl group having 3-7 carbon atoms in the ring and having the formula:

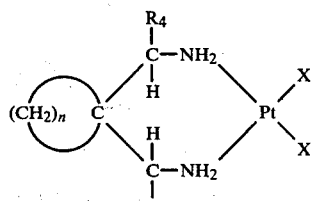

wherein n is 2 to 7 and wherein R$_3$ and R$_4$ independently of each other are selected from the group consisting of hydrogen, an alkyl group having 1-20 carbon atoms, an aryl group or an aralkyl group having 1-20 carbon atoms in the alkyl group and X is an anionic group, providing that when X is either chlorine or malonato, R$_1$, R$_2$, R$_3$ and R$_4$ are not each H; when X is chlorine and R$_1$ and R$_2$ are each H, R$_3$ and R$_4$ are not each methyl; when X is chlorine and R$_1$ and R$_2$ are each methyl; R$_3$ and R$_4$ are not each H, and when X is chlorine R$_1$ is hydrogen and R$_2$ is methyl, R$_3$ and R$_4$ are not each hydrogen.

2. Platinum-diamine complexes having the formula:

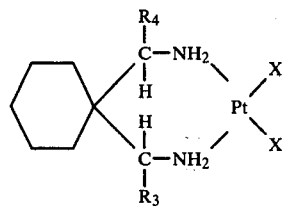

wherein R$_3$ and R$_4$ independently of each other are selected from the group consisting of hydrogen, alkyl group having 1-20 carbon atoms, an aryl group or an aralkyl group having 1-20 carbon atoms in the alkyl group and X is an anionic group, selected from the group consisting of chlorine, bromine, iodine, sulphate, phthalate, acetate, oxalate, malonate, substituted malonate, carboxylate, and isocitrate.

3. Cis-dichloro-1,1-di(aminomethyl)cycloalkyl platinum(II) having the formula:

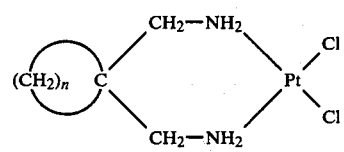

wherein n is 3 to 7.

4. Cis-diiodo-1,1-di(aminomethyl)cyclohexane platinum(II) having the formula:

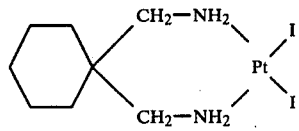

5. Cis-cyclopentamethylene malonato-1,1-di(aminomethyl)cyclohexane platinum(II) having the formula:

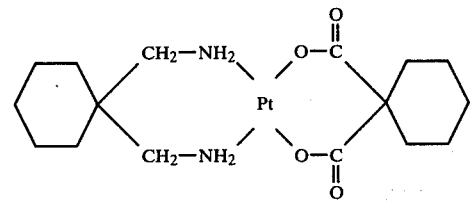

6. Cis-dichloro-(2-methyl-2-ethyl)-1,3-propane diamine platinum(II) having the formula:

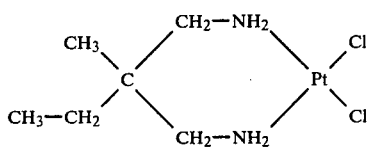

7. Cis-dichloro-2,2-diethyl-1,3-propane diamine platinum(II) having the formula:

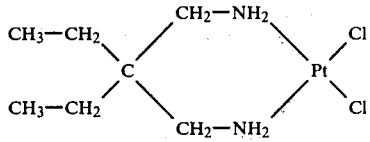

8. Cis-dichloro-1,1-di(aminomethyl)cyclopentane platinum(II) having the formula:

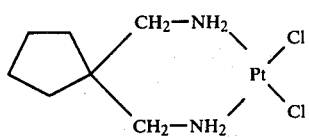

9. Cis-1,1-di(aminomethyl)cyclohexane platinum(II) sulphate having the formula:

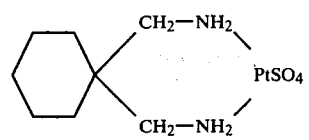

10. Cis-dichloro-1,1-di(aminomethyl)cyclobutane platinum(II) having the formula:

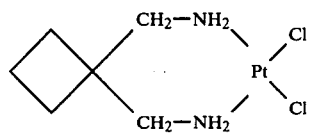

11. Cis-dichloro-2,2-dibenzyl-1,3-propane diamine platinum(II) having the formula:

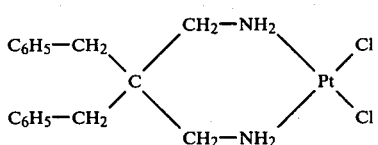

12. Cis-dichloro-2,2-diisopropyl-1,3-propane diamine platinum(II) having the formula:

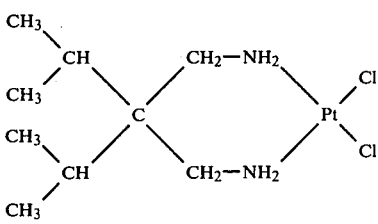

13. Cis-4-carboxyphtalato-1,1-di(aminomethyl)cyclohexane platinum(II) having the formula:

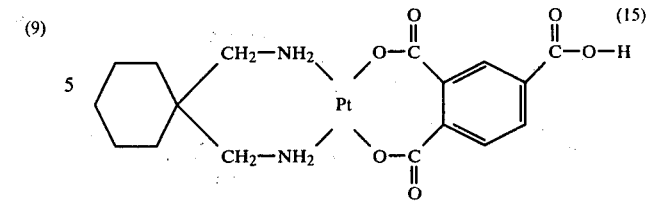

14. Cis-1,1-di(aminomethyl)-cyclohexane-bis(chloroacetato) platinum(II) having the formula:

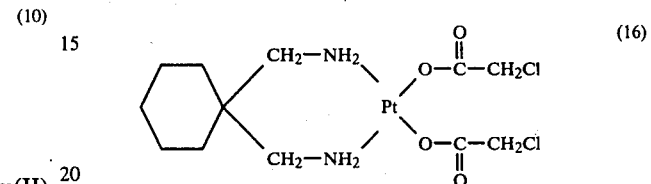

15. Cis-2,2-diethyl-1,3-propanediamine platinum(II) sulphate having the formula:

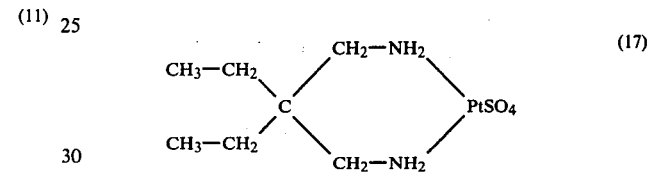

16. Cis-1,1-di(aminomethyl)cyclohexanemalonato platinum(II) having the formula:

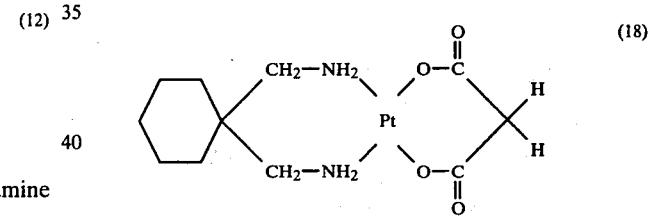

17. Cis-1,1-di(aminomethyl)cyclohexanehydroxymalonato platinum(II) having the formula:

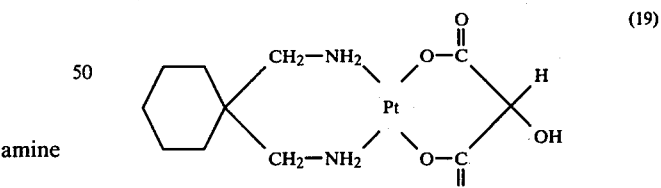

18. Cis-2,2-diethyl-1,3-diaminopropane 2-ethylmalonato platinum(II) having the formula:

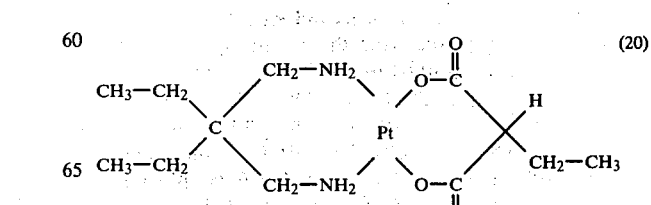

19. Cis-2,2-diethyl-1,3-diaminopropane 2-hydroxymalonato platinum(II) having the formula:

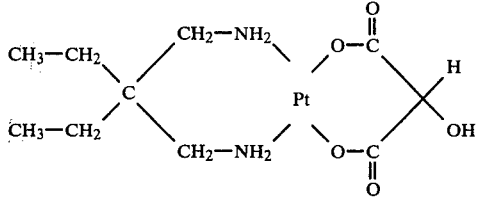

20. Cis-1,1-di(aminomethyl)cyclhexane 2-ethylmalonato platinum(II) having the formula:

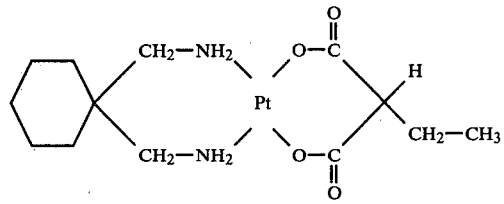

21. Cis-2,2-diethyl-1,3-diaminopropane 2-hydroxymalonato platinum(II) sodium salt, having the formula:

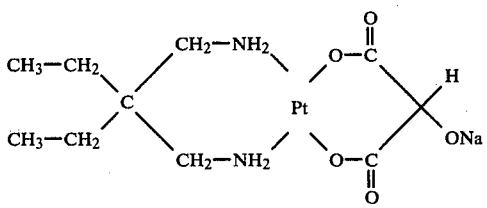

22. Cis-1,1-di(aminomethyl)cyclohexane 1,1-cyclobutanedicarboxylato platinum(II) having the formula:

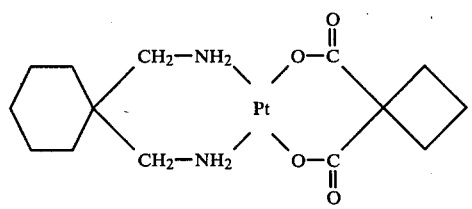

23. Cis-2,2-diethyl-1,3-diaminopropane 1,1-cyclobutanedicarboxylato platinum(II) having the formula:

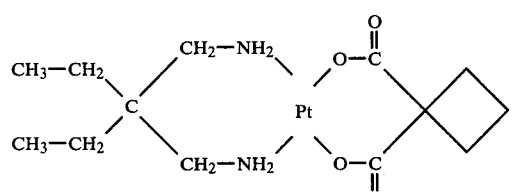

24. Cis-1,1-di(aminomethyl)cyclohexane platinum(II) isocitrate having the formula:

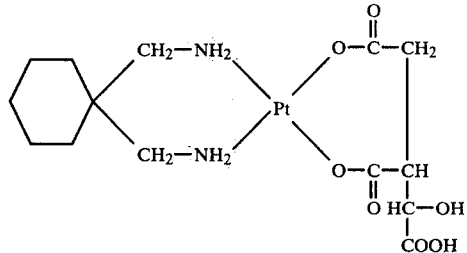

25. Cis-dichloro-1,1-di(aminomethyl)cyclohexane platinum(II) having the formula:

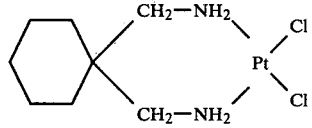

26. A pharmaceutical composition comprising a liquid or solid carrier and an amount of at least one of the compounds described in claim 1, 2, 3, 4, 5, 6, 7, 8, 9, 10, 11, 12, 13, 14, 15, 16, 17, 18, 19, 20, 21, 22, 23, 24 or 25 sufficient to treat malignant tumors in mice.

27. A method of treating malignant tumors in mice which consists of administering a therapuetically effective amount of the composition described in claim 1, 2, 3, 4, 5, 6, 7, 8, 9, 10, 11, 12, 13, 14, 15, 16, 17, 18, 19, 20, 21, 22, 23, 24 or 25 to mice having malignant tumors.

28. A pharmaceutical composition comprising a liquid or solid carrier and an amount sufficient to treat malignant tumors in mice of at least one of a platinum diamine complex having the formula:

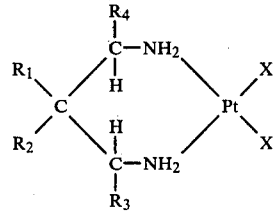

wherein $R_1$ and $R_2$ independently of each other may be selected from the group consisting of hydrogen, an alkyl group having 1-20 carbon atoms, a cycloalkyl group having from 3-7 carbon atoms in the ring, an aralkyl group and an aryl group having 1-20 carbon atoms, whereas $R_1$ and $R_2$ together may form a cycloalkyl group having 3-7 carbon atoms in the ring and having the formula:

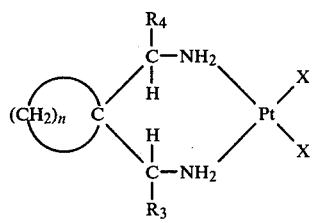

wherein n is 2 to 7 and wherein $R_3$ and $R_4$ independently of each other are selected from the group consisting of hydrogen, an alkyl group having 1-20 carbon atoms, an aryl group or an aralkyl group having 1-20 carbon atoms in the alkyl group and X is an anionic group.

29. A method of treating malignant tumors in mice which consists of administering a therapeutically effective amount of the composition described in claim 28 to mice having malignant tumors.

UNITED STATES PATENT AND TRADEMARK OFFICE
CERTIFICATE OF CORRECTION

PATENT NO. : 4,410,544                            Page 1 of 3

DATED : October 18, 1983

INVENTOR(S) : Berg et al.

It is certified that error appears in the above—identified patent and that said Letters Patent is hereby corrected as shown below:

Col. 2, line 19, before "mice" insert --malignant tumors in--;

Col. 6, line 61, "In" should be --It--;

Col. 7, line 45, after "20.65 g" insert --of--;

Col. 8, line 15, after "18.55." insert --Found:--;

Col. 8, line 32, after "17.89." insert --Found:--;

Col. 10, line 8, "has" should be --had--;

Col. 10, line 34, after "4.23;" "H" should be --N--;

Col. 10, line 35, after "4.21;" "H" should be --N--;

UNITED STATES PATENT AND TRADEMARK OFFICE
CERTIFICATE OF CORRECTION

PATENT NO. : 4,410,544
DATED : October 18, 1983
INVENTOR(S) : Berg et al.

It is certified that error appears in the above—identified patent and that said Letters Patent is hereby corrected as shown below:

Page 1, Item 54, line 5, "TUMOR" should be --TUMORS--;

Page 1, Item 54, line 6, after "MICE" insert --, AS WELL AS A MEDICINE THUS FORMED--;

Page 1, Item 73, lines 3-4, "Toegespastnatuurwetenschappeliukonderzoek" should be Toegepastnatuurwetenschappelijk Onderzoek--;

Page 1, Item 73, last line, after "Stolberglaan" insert --The Hague--;

Col. 1, lines 5 and 6, "TUMOR IN MICE" should be --TUMORS IN MICE, AS WELL AS A MEDICINE THUS FORMED--;

Col. 1, line 12, before "mice" insert --malignant tumors in--;

UNITED STATES PATENT AND TRADEMARK OFFICE
CERTIFICATE OF CORRECTION

PATENT NO. : 4,410,544

DATED : October 18, 1983

INVENTOR(S) : Berg et al.

It is certified that error appears in the above-identified patent and that said Letters Patent is hereby corrected as shown below:

Col. 10, line 44, "H: 6.68" should be --N: 6.68--;

Col. 10, line 60, after "4.59;" "H" should be --N--;

Col. 10, line 61, after "4.54;" "H" should be --N--;

Col. 13, line 26, after "4.59;" "H" should be --N--;

Col. 13, line 27, "H: 5.0" should be --N: 5.0--;

Col. 17, line 14 "cyclhexane" should be --cyclohexane--.

Signed and Sealed this

Tenth Day of April 1984

[SEAL]

Attest:

GERALD J. MOSSINGHOFF

Attesting Officer    Commissioner of Patents and Trademarks